(12) United States Patent
Maleev et al.

(10) Patent No.: US 9,995,850 B2
(45) Date of Patent: Jun. 12, 2018

(54) SYSTEM, METHOD AND APPARATUS FOR POLARIZATION CONTROL

(71) Applicant: KLA-Tencor Corporation, Milpitas, CA (US)

(72) Inventors: Ivan Maleev, Pleasanton, CA (US); Donald Pettibone, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 711 days.

(21) Appl. No.: 14/296,425

(22) Filed: Jun. 4, 2014

(65) Prior Publication Data

US 2014/0361152 A1 Dec. 11, 2014

Related U.S. Application Data

(60) Provisional application No. 61/831,950, filed on Jun. 6, 2013.

(51) Int. Cl.
*G01N 21/21* (2006.01)
*G01N 21/01* (2006.01)
(Continued)

(52) U.S. Cl.
CPC ........... *G02B 1/02* (2013.01); *G01N 21/8806* (2013.01); *G01N 21/9501* (2013.01);
(Continued)

(58) Field of Classification Search
CPC .......... G02B 1/02; G02B 1/08; G02B 5/3083; G02B 5/3008; G02B 27/286; G01N 21/8806; G01N 2021/8848; G01N 21/9501
See application file for complete search history.

(56) References Cited

U.S. PATENT DOCUMENTS 3,758,201 A * 9/1973 MacNeille ............... A61B 3/02
351/159.56
5,414,510 A * 5/1995 Schultz .................... G01H 9/00
356/432
(Continued)

FOREIGN PATENT DOCUMENTS

JP 2010192914 A 9/2010
KR 1020120000088 A 1/2012

OTHER PUBLICATIONS

Jenoptik. Liquid Crystal Spatial Light Modulators description. http://www.jenoptik.com/en-liquid-crystal-spatial-light-modulators. (Downloaded on Jun. 6, 2014).
(Continued)

Primary Examiner — John Lee
(74) Attorney, Agent, or Firm — Suiter Swantz pc llo

(57) ABSTRACT

A polarization control device includes a first wave plate having a first surface profile and a second wave plate having a second surface profile complementary to the first surface profile. The optical axis of the first wave plate is orthogonal to the optical axis of the second wave plate. The first wave plate and the second wave plate are positioned to align the first surface profile with the second surface profile and maintain a constant thickness across the polarization control device. The first wave plate and the second wave plate may control polarization rotation as a continuous function of transverse position across a pupil plane of an optical system. The first wave plate and the second wave plate are separated by a sufficiently small distance so as to limit wave front distortion below a selected level.

33 Claims, 12 Drawing Sheets

(51) Int. Cl.
*G02B 1/02* (2006.01)
*G02B 27/28* (2006.01)
*G02B 5/30* (2006.01)
*G01N 21/88* (2006.01)
*G01N 21/95* (2006.01)

(52) U.S. Cl.
CPC ......... *G02B 5/3083* (2013.01); *G02B 27/286* (2013.01); *G01N 2021/8848* (2013.01)

(56) References Cited

U.S. PATENT DOCUMENTS

| | | | | |
|---|---|---|---|---|
| 5,635,829 | A * | 6/1997 | Hamada | G01R 15/247 324/117 R |
| 6,034,776 | A | 3/2000 | Germer et al. | |
| 6,072,628 | A * | 6/2000 | Sarayeddine | G02B 27/283 359/485.02 |
| 6,320,699 | B1 * | 11/2001 | Maeda | G02B 5/3083 359/637 |
| 2002/0191288 | A1 * | 12/2002 | Gruner | G03F 7/70058 359/489.05 |
| 2004/0092045 | A1 * | 5/2004 | Bultman | G01N 21/211 438/16 |
| 2004/0125373 | A1 * | 7/2004 | Oldenbourg | G02B 21/0092 356/364 |
| 2006/0065820 | A1 | 3/2006 | Nagai | |
| 2006/0072807 | A1 * | 4/2006 | Bultman | G01N 21/211 382/149 |
| 2006/0092398 | A1 * | 5/2006 | McCarthy | G02B 17/0892 355/71 |
| 2006/0203214 | A1 * | 9/2006 | Shiraishi | G02B 27/28 355/52 |
| 2006/0262236 | A1 * | 11/2006 | Abileah | G02F 1/13338 349/12 |
| 2008/0007726 | A1 | 1/2008 | Fairley et al. | |
| 2008/0198456 | A1 * | 8/2008 | Sharp | G02B 27/288 359/489.07 |
| 2009/0015761 | A1 * | 1/2009 | Stockham | G06F 3/0412 349/96 |
| 2009/0115989 | A1 * | 5/2009 | Tanaka | G03F 7/70566 355/71 |
| 2009/0296066 | A1 * | 12/2009 | Fiolka | G02B 27/286 355/71 |
| 2010/0045957 | A1 | 2/2010 | Fiolka et al. | |
| 2010/0118288 | A1 * | 5/2010 | Van De Kerkhof | G01M 11/0264 355/71 |
| 2010/0177293 | A1 * | 7/2010 | Fiolka | G02B 1/08 355/67 |
| 2011/0007316 | A1 * | 1/2011 | De Wit | G01N 21/47 356/365 |
| 2011/0228247 | A1 * | 9/2011 | Mulder | G03F 7/70116 355/71 |
| 2012/0092669 | A1 * | 4/2012 | Fiolka | G01M 11/0257 356/365 |
| 2013/0039460 | A1 * | 2/2013 | Levy | G01N 21/211 378/44 |
| 2014/0361152 | A1 * | 12/2014 | Maleev | G02B 27/286 250/225 |

OTHER PUBLICATIONS

Tricard, Marc, Paul Dumas, and Joe Menapace. Continuous Phase Plate Polishing Using Magnetorheological Finishing. pp. 1-4. QED Technologies, Rochester, NY, USA and Lawrence Livermore National Laboratories, Livermore, CA, USA. (No date available).
Menapace, Joseph A., Sham N. Dixit, Francois Y. Genin, and Wayne F. Brocious. Magnetorheological Finishing for Imprinting Continuous Phase Plate Structure onto Optical Surfaces. Laser-Induced Damage in Optical Materials. Downloaded from http://spiedigitallibrary.org on Dec. 14, 2012. pp. 220-230. vol. 5273. Bellingham, WA, USA.
Newport. Properties of Optical Materials. http://www.newport.com/Optical-Materials/144943/1033/content.aspx. (Downloaded on Jun. 6, 2014).

* cited by examiner

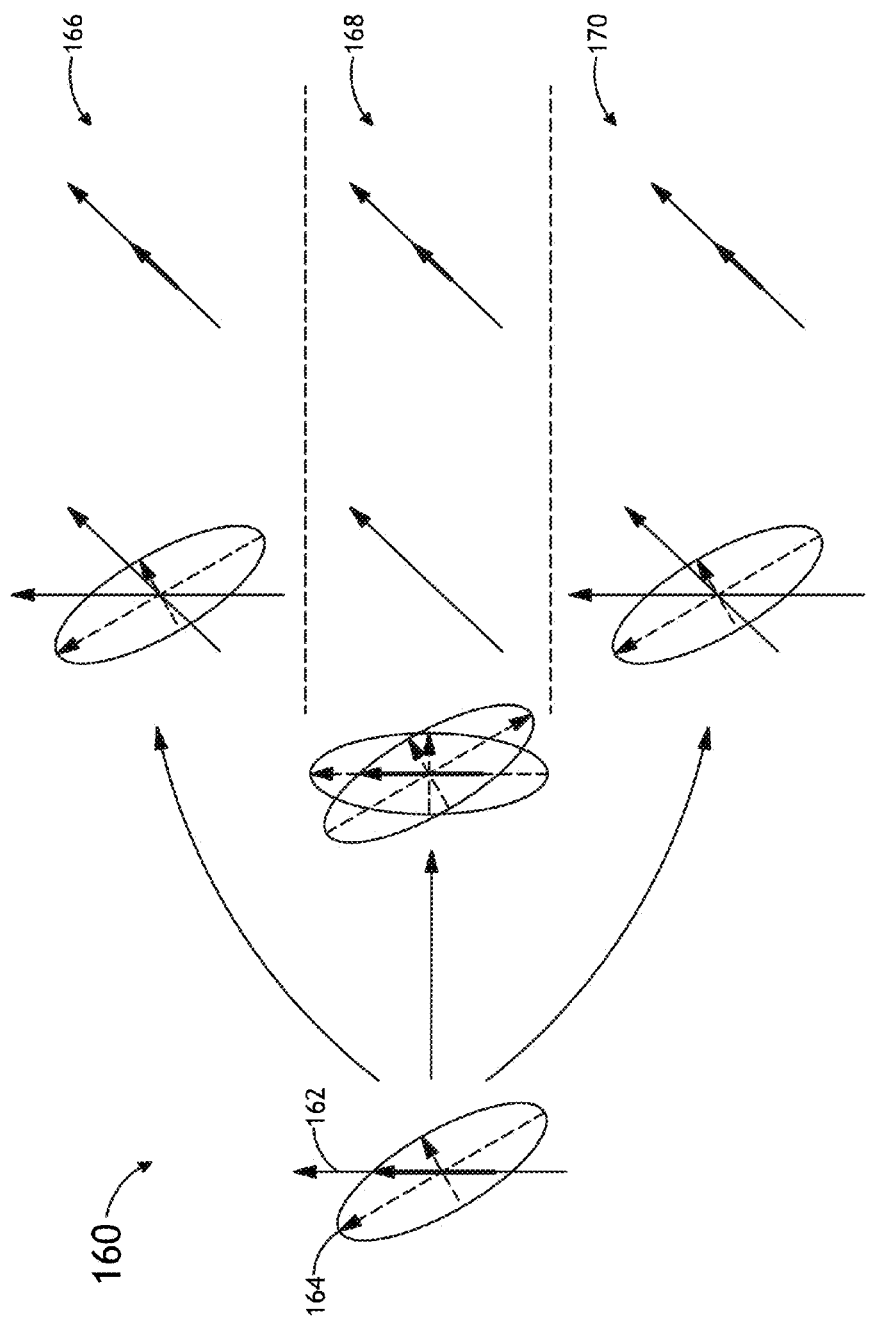

SYSTEM, METHOD AND APPARATUS FOR POLARIZATION CONTROL

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled POLARIZATION CORRECTION DEVICE FOR HIGH NA UV OPTICAL SYSTEMS, naming IVAN MALEEV as inventor, filed Jun. 6, 2013, Application Ser. No. 61/831,950.

TECHNICAL FIELD

The present invention generally relates to polarization control in an optical system. In particular, the present invention relates to polarization control in a high NA inspection system.

BACKGROUND

As the demand for integrated circuits having ever-smaller device features continues to increase, the need for improved substrate inspection systems continues to grow. One aspect of inspection tool operation includes the control of polarization within the optical pathway of the inspection system implemented in order to analyze various aspects of defect, particle or surface features of a given sample, such as a semiconductor wafer. Traditional polarization control devices include electronically-controlled spatial light modulator devices. Typical spatial light modulators utilize liquid crystals, which currently are not suitable with UV light (λ<300 nm). In addition, previous spatial control of polarization within an optical pathway provides for discrete changes in polarization retardation. Such systems may result in a significant amount of stray light production due to scattering from pixel boundaries.

It is further noted that any polarization control mechanism must compete with other optical requirements, such as transmission, field of view, high numerical aperture, and control of aberrations. For example, an all-refractive element based optical system may result in a high number of such elements, which are all necessary to control different types of aberrations, which results in reduced system transmission, which, in turn, leads to higher cost. In addition, other optical designs, such as a parabolic mirror or simple Swartzschild objective, have intrinsic optical limitations, which, for example, may lead to various degrees of polarization aberration.

Another aspect of inspection tool operation includes the control of point spread function (PSF) at an imaging detector. Typical optical systems minimize PSF size by increasing numerical aperture (NA) and reducing aberrations in an effort to obtain a PSF as close to the diffraction limit as possible. However, in applications related to detecting small surface defects via light scattering techniques, the maximization of signal-to-noise ratio (SNR). One approach typically used to maximize SNR is to minimize unwanted noise originating from light scattered by a surface, while maintaining (or increasing) light from a defect of interest. Typically, this can accomplished via control of the transmitted polarization, and by mechanically limiting an open aperture. Transmission and suppression of polarizations of interest over a pupil plane may be controlled with single or multiple mechanical polarization elements in a pupil plane, with transmitted light having varying polarization across the pupil plane. However, such measures result in degrading PSF away from the diffraction limit. Therefore, it would be desirable to provide a system and method for curing defects such as those of the identified above.

SUMMARY OF THE INVENTION

A polarization control apparatus is disclosed, in accordance with an illustrative embodiment of the present invention. In one illustrative embodiment, the polarization control apparatus may include a first wave plate having a first surface profile and a second wave plate having a second surface profile complementary to the first surface profile. In one embodiment, the optical axis of the first wave plate is substantially orthogonal to the optical axis of the second wave plate. In another embodiment, the first wave plate and the second wave plate are positioned so as to substantially align the first surface profile with the second surface profile and maintain a constant thickness of an assembly of the first wave plate and second wave plate. In another embodiment, the first wave plate and the second wave plate are configured to control polarization rotation as a continuous function of transverse position across a pupil plane of an optical system. In another embodiment, the first profile of the first wave plate is separated from the second profile of the second wave plate by a selected distance so as to limit wave front distortion of illumination passing through the first wave plate and second wave plate below a selected level.

In another illustrative embodiment, polarization control apparatus may include a single wave plate having a surface profile configured to control polarization rotation as a continuous function of transverse position across a pupil plane of an optical system.

An optical system for controlling polarization is disclosed, in accordance with an illustrative embodiment of the present invention. In one illustrative embodiment, the optical system may include an illumination source configured to illuminate a surface of a sample, a set of collection optics configured to collect illumination from the surface of a sample and a polarization control device positioned substantially at a pupil plane of the optical system. In one embodiment, the polarization control device may include a first wave plate having a first surface profile and a second wave plate having a second surface profile complementary to the first surface profile. In one embodiment, the optical axis of the first wave plate is substantially orthogonal to the optical axis of the second wave plate. In another embodiment, the optical axis of the first wave plate and the optical axis of the second wave plate are substantially orthogonal to a direction of illumination propagation through the polarization control device. In another embodiment, the first wave plate and the second wave plate are positioned so as to substantially align the first surface profile with the second surface profile and maintain a constant thickness of an assembly of the first wave plate and second wave plate. In another embodiment, the first wave plate and the second wave plate are configured to control polarization rotation as a function of transverse position in a pupil plane of the optical system. In another embodiment, the optical system includes a linear polarizer configured to receive illumination transmitted through the polarization control device and a sensor configured to detect illumination transmitted through the linear polarizer.

An optical system for controlling point spread function is disclosed, in accordance with an illustrative embodiment of the present invention. In one illustrative embodiment, the optical system includes an illumination source configured to illuminate a surface of a sample, a set of collection optics configured to collect illumination from the surface of a sample, a detector including a plurality of pixels and a point spread function control device positioned substantially at a pupil plane of the optical system. In one embodiment, the point spread function control devices may include a first wave plate having a first surface profile and a second wave plate having a second surface profile complementary to the first surface profile. In another embodiment, the first wave plate and the second wave plate are positioned so as to substantially align the first surface profile with the second surface profile and maintain a constant thickness of an assembly of the first wave plate and second wave plate. In another embodiment, the first wave plate and the second wave plate are configured to control at least one of polarization rotation and degree of coherence as a continuous function of transverse position across the pupil plane in order to modify the point spread function of illumination in order to enhance an amount of energy received by one or more pixels of the detector.

In another illustrative embodiment, the optical system for controlling point spread function may include an illumination source configured to illuminate a surface of a sample, a set of collection optics configured to collect illumination from the surface of a sample, a detector including a plurality of pixels and a point spread function control device positioned substantially at a pupil plane of the optical system. In one embodiment, the point spread function control devices may include a first wave plate having a first surface profile and a second wave plate having a second surface profile complementary to the first surface profile. In one embodiment, the first wave plate and the second wave plate are positioned so as to substantially align the first surface profile with the second surface profile and maintain a constant thickness of an assembly of the first wave plate and second wave plate. In one embodiment, the first wave plate and the second wave plate are configured to impart an optical delay as a continuous function of transverse position across a pupil plane of an optical system in order to modify the point spread function of illumination in order to enhance an amount of energy received by one or more pixels of the detector.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 1F illustrates a conceptual illustration of the conversion of elliptically polarized background signal into linear polarized light, in accordance with one embodiment of the present invention.

DETAILED DESCRIPTION OF THE INVENTION

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention. Reference will now be made in detail to the subject matter disclosed, which is illustrated in the accompanying drawings.

Referring generally to FIGS. 1A through 5E, an apparatus and system for polarization and/or point spread function control in an optical system are described, in accordance with one or more embodiments of the present disclosure.

Embodiments of the present disclosure are directed to one or more polarization control devices suitable for controlling polarization as a continuous function across the pupil plane of an optical inspection system, such as, but not limited to, a high numerical aperture (high-NA) ultraviolet (UV) inspection system. The polarization control device of the present disclosure may allow for the correction of aberrations created by one or more optical elements of the particular optical system. In addition, the polarization control device may further provide for the enhancement of the signal-to-noise ratio via the suppression of an unwanted signal (e.g., surface haze) relative to a desired signal (e.g., scattering signal from particle). Embodiments of the polarization control device of the present disclosure accomplish such spatially continuous polarization control across the pupil plane of an optical system via the implementation of two phase plates with complementary surfaces, described further herein. The applications of such a device in a UV inspection system, for example, include the ability to relax the requirements of other, more complex, optical components. For instance, the polarization control outlined in the present disclosure may allow for the use of catadioptric systems or other optical designs, which substantially distort input polarization distributions over NA.

Additional embodiments of the present disclosure are directed to one or more point spread function control devices suitable for controlling the point spread function of illumination impinging on a detector array of a detector. The point spread function control devices described herein are capable of modifying the point spread function of an optical system through the modulation of phase and/or degree of coherence over the pupil plane of an optical system. This capability may serve to enhance or maximize the energy received by a single pixel in a detector array.

Figure 1A:
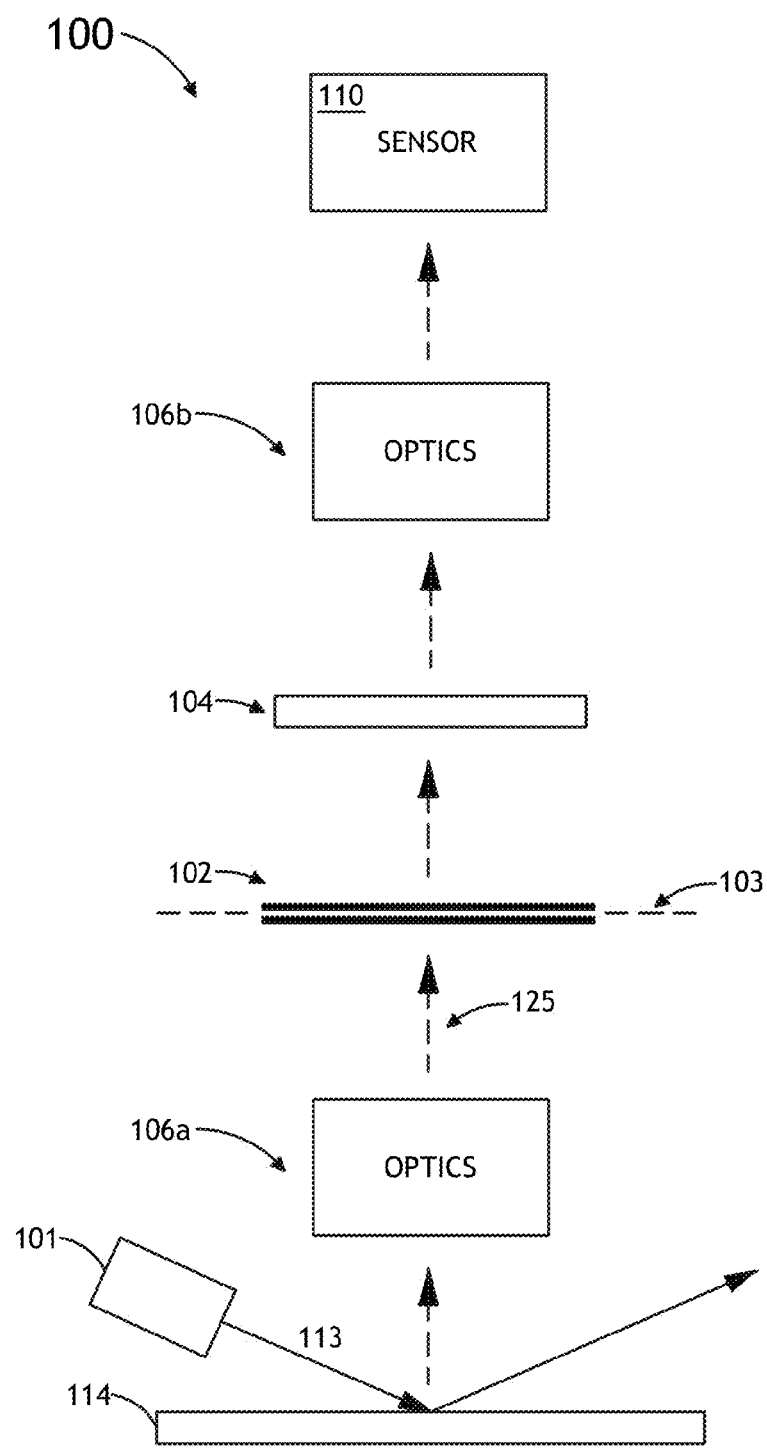
FIG. 1A illustrates a block diagram view of a system implementing a polarization control device, in accordance with one embodiment of the present invention.

FIG. 1A illustrates a conceptual block diagram view of a system 100 having polarization control capabilities, in accordance with one or more embodiments of the present disclosure.

In one embodiment, the system 100 includes an illumination source 101. In one embodiment, the illumination source 101 is configured to illuminate the surface of the sample 114 with illumination 113. The sample 114 may include any substrate, wafer or specimen known in the art, such as a semiconductor wafer. The illumination source 101 may include any illumination source known in the art of sample inspection. For example, the illumination source 101 may include, but is not limited to, a narrow band light source (e.g., one or more lasers). By way of another example, the illumination source 101 may include, but is not limited to, a broad band light source (e.g., laser-sustained plasma light source, discharge lamp and the like). Further, the illumination source 101 may illuminate the surface of the sample 114 with illumination 113 of any spectral range known in the art of sample inspection. For example, the illumination source 101 may be configured to illuminate a portion of the sample 114 with one or more of ultraviolet or visible light. In another embodiment, the system 100 includes a set of illumination optics (not shown) for directing and/or focusing illumination 113 emitted by the illumination source 101 onto a selected portion of the surface of the sample 114. For example, the set of illumination optics may include, but is not limited to, one or more lenses, one or more mirrors, one or more beam splitters, one or more filters and the like.

It is noted herein that the optical system 100 may include any optical inspection system known in the art. In one embodiment, the inspection system may include, but is not limited to, a reflective-based inspection system (e.g., system 200, system 300 and like systems). Examples of reflective-based systems are described further herein. In another embodiment, the optical system 100 may include a refractive-based inspection system (e.g., system 500). In one embodiment, the optical system 100 may include, but is not limited to, a high-NA inspection system. In another embodiment, the optical system 100 may include a high-NA ultraviolet inspection system.

In another embodiment, the system 100 includes a set of collection optics 106a, 106b. In one embodiment, the set of collection optics 106a, 106b are configured to collect illumination from the surface (e.g., light scattered from one or more defects, light reflected from sample surface and the like) of the sample 114. The collection optics 106a, 106b may include any set of collection optics known in the art of sample inspection. For example, the collection optics 106a, 106b may include, but are not limited to, a Schwarzchild objective with tube lens, a Schwarzchild objective with an afocal lens, one or more parabolic collectors and the like. In another embodiment, the collection optics 106a, 106b may include a set of refractive optics. For example, the collection optics 106a, 106b may include, but are not limited to, a catadioptric objective. It is noted herein that particular implementations of inspection architecture are described in greater detail further herein.

In one embodiment, the optical system 100 includes a polarization control device 102, in accordance with one embodiment of the present disclosure. In one embodiment, the polarization control device 102 is positioned at the pupil plane 103 of the optical system 100. As noted in greater detail further herein, the polarization control device 102 is constructed so as to control polarization rotation continuously as a function of position across the pupil plane 103 of the optical system 100. In one embodiment, such polarization control across the pupil plane 103 may be used to correct polarization aberrations in the optical system 100. In another embodiment, the polarization control across the pupil plane 103 may be used to alter and/or suppress an undesirable polarization distribution from the sample 114.

In another embodiment, the optical system 100 includes a linear polarizer 104. In one embodiment, the linear polarizer 104 may also be substantially positioned at the pupil plane 103. In one embodiment, the linear polarizer 104 may be used to analyze the polarization of light following the polarization operations imparted to the light (as a function of x,y position) by the polarization control device 102.

In another embodiment, the system 100 includes a sensor 110. In one embodiment, the sensor 110 is configured to detect illumination from the surface of the sample 114 upon transmission of the illumination through at least the polarization control device 102 and the polarizer 104. The sensor 110 may include any optical sensor known in the art of sample inspection. For example, the sensor 110 may include, but is not limited to, one or more CCD detectors. By way of another example, the sensor 110 may include, but is not limited to, one or more TDI-CCD detectors.

Figure 1B:
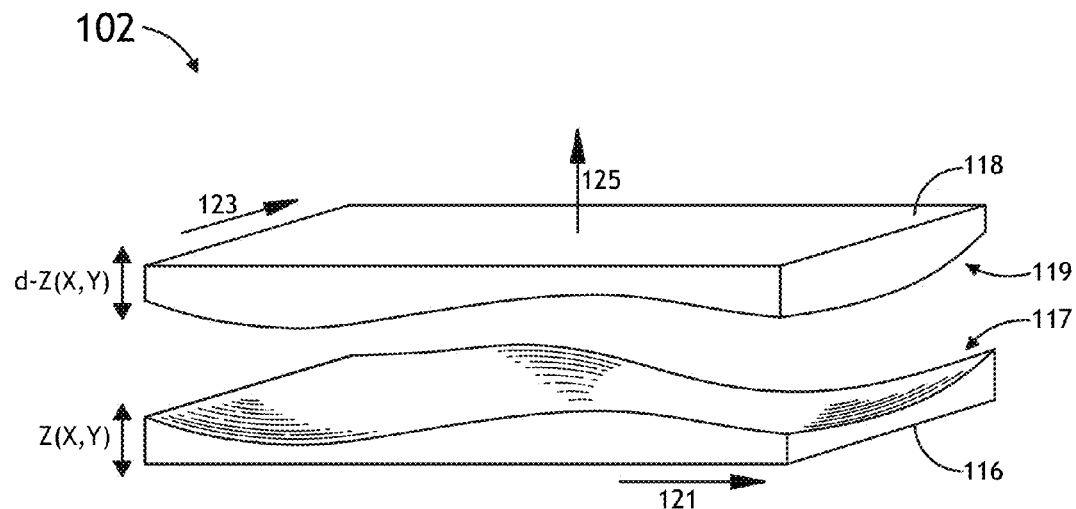
FIG. 1B illustrates an exploded schematic view of the polarization control device, in accordance with one embodiment of the present invention.
Figure 1C:
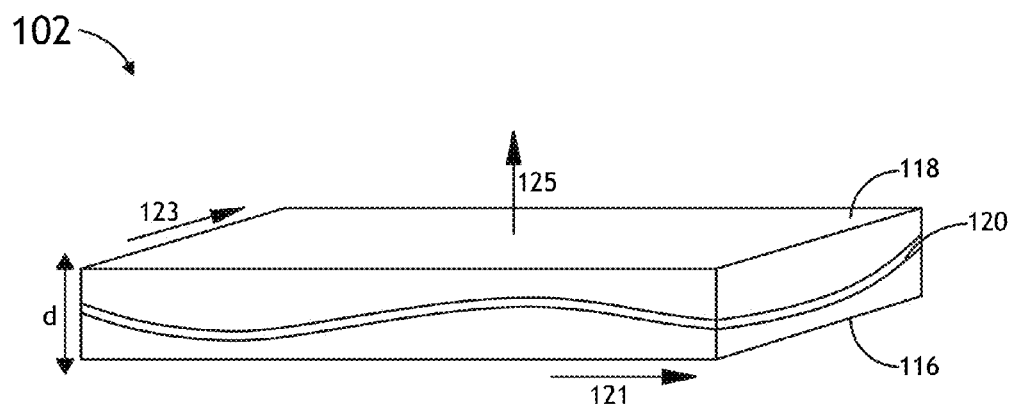
FIG. 1C illustrates an assembled schematic view of the polarization control device, in accordance with one embodiment of the present invention.

FIGS. 1B and 1C illustrate simplified schematic views of the dual-plate polarization control device 102, in accordance with one or more embodiments of the present disclosure. FIG. 1B illustrates a simplified exploded schematic view of the polarization control device 102, in accordance with one or more embodiments of the present invention. FIG. 1C illustrates a simplified assembled schematic view of the polarization control device 102, in accordance with one or more embodiments of the present invention.

In one embodiment, the polarization control device 102 is placed in the pupil plane 103 of the optical system 100, as shown in FIG. 1A. In one embodiment, the optical axis 121 of the first plate 116 is oriented substantially orthogonal to the optical axis 123 of the second plate 118. In another embodiment, both the optical axis 121 of the first plate 116 and the optical axis 123 of the second plate 118 are oriented substantially orthogonal to the direction 125 of illumination transmission through the polarization control device 102. It is noted herein that the orthogonal alignment of the optical axes 121, 123 of the first and second plates 116, 118 provides for birefringence in the combined plate polarization control device 102.

In one embodiment, the first wave plate 116 and the second wave plate 118 are configured to continuously control polarization rotation as a function of transverse position in the pupil plane 103 of an optical system 100.

In one embodiment, the first wave plate 116 and the second wave plate 118 control polarization rotation in a continuous manner (i.e., non-discrete) across the pupil plane 103 of an optical system by controlling the level of retardance continuously across the pupil plane 103. In this regard, the first wave plate 116 and the second wave plate 118 serve to continuously control the phase delay between polarization states (e.g., s-polarization and p-polarization) of light passing through the polarization control device 102, with the amount of the delay being a function of the position of the light incident on the polarization control device 102. As shown in FIGS. 1B and 1C, the phase delay is controlled as a function of position across the pupil plane by controlling the thickness of one or more individual plates 116, 118 as a function of transverse position (e.g., x, y position) across the pupil plane 103.

By controlling the amount of imparted polarization rotation as a function of position across the pupil plane 103, the polarization control device 102 may form a continuous 'polarization map' across the pupil plane 103. It is noted herein that the utilization of continuous polarization control over NA is particularly advantageous as it avoids scattering from discrete polarizing elements, which is commonly encountered in discrete polarization control schemes.

In one embodiment, the polarization control device 102 includes a first wave plate 116 having a first surface profile 117. In another embodiment, the polarization control device 102 includes a second wave plate 118 having a second surface profile 119. In one embodiment, the profile 119 of the second wave plate 118 is complementary to the profile 117 of the first wave plate 116. The complementary surface profiles 117, 119 of the first wave plate 116 and the second wave plate 118 allow for close alignment of the first wave plate 116 and second wave plate 118. In this regard, the complementary surface profiles 117, 119 of the first wave plate 116 and the second wave plate 118 allow the wave plates 116, 118 to be aligned in a manner such that a combined assembly of the first wave plate 116 and second wave plate 118 has a substantially constant thickness d, as shown in FIG. 1C. It is noted herein that the combination of the first wave plate 116 and the second wave plate 118 having a substantially constant thickness (and spacing between plates) aids in limiting distortion(s) of the wave front passing through the polarization control device 102.

In another embodiment, upon forming the complementary surfaces 117, 119, the first plate 116 and second plate 118 may be positioned proximate to each other, as shown in FIG. 1C. In one embodiment, the surface profile 117 of the first wave plate 116 is separated from the surface profile 119 of the second wave plate 118 by a selected nominal distance that is sufficiently small so as to limit wave front distortion of illumination passing through the first wave plate 116 and second wave plate 118 (e.g., limit below a selected level). For example, the surface profile 117 of the first plate 116 an the surface profile 119 of the second plate 118 may be positioned sufficiently close to teach other so that the local tilt of the surfaces 117, 119 does result in local wave front shift and corresponding distortions.

In another embodiment, the surface 117 of the first plate 116 and the surface 119 of the second plate 118 may be operably coupled to each other. In one embodiment, the surface 117 of the first plate 116 and the surface 119 of the second plate 118 may be affixed (e.g., affixed using glue, epoxy and the like) to one another in order to minimize light loss in the interface 120. In another embodiment, an index-matching fluid may be disposed in the interface 120 between the surface 117 of the first plate 116 and the surface 119 of the second plate 118. In another embodiment, the surface 117 of the first plate 116 and the surface 119 of the second plate 118 may be mechanically coupled (e.g., clamp) to each other in order to minimize light loss in the interface 120.

It is noted herein that the local shift of the wave front is defined by the local surface tilt at the interface between two plates 116, 118. For example, in the case of magnesium fluoride ($MgF_2$) where the characteristic distance for the change of phase delay by $2\pi$ in x-direction is 10 mm with a surface profile described by a sine function, the surface may display a period of 20 mm and an amplitude of 5.244 μm ($2\pi*1.6694$). This then corresponds to a profile function $z(x,y)$ (measured in μm) as below:

$$z(x, y) = 5.244 * \sin\left(\frac{2\pi x}{20,000}\right)$$

Further, the derivative of the profile function is given by:

$$z'(x, y) = 5.244 * \frac{\pi}{10,000} \cos\left(\frac{\pi x}{10,000}\right)$$

As such, the maximum local tilt in this example is:

$$T = 5.244 * \frac{\pi}{10,000}$$

The above tilt corresponds approximately to 1.65 mrad. With an interface 120 index of refraction of n, and beam tilt values defined by Snell's law, for a normal incidence beam at the exit of first plate 116, the angle G of the output beam with respect to the normal is given by $\sin(G)=\sin(T)*n_e/n$. For instance, in the case of an air interface 120, G is approximately 2.3 mrad. Upon entering the second plate 118, the angle P of the beam with respect to the normal of the interface 120 surface will be defined by $\sin(P)=\sin(G)*n/n_e=\sin(T)$. Inside the interface 120, the deviation of a beam from normal to the external plate surface corresponds to (G−T) or approximately 0.66 urad. In the case where the interface 120 thickness is p=100 μm, the approximate local shift of the wave front is $p*\sin(G-T)$ or approximately 66 nm. It is further noted that a reduction below 1 nm may be possible with index matching interface 120 material of n~1.4 and/or reduced interface 120 thickness (e.g., 1 μm interface results in local shift of 0.7 nm).

In one embodiment, the complementary surface profiles 117, 119 may be created by treating the surface of plates 116 and 118 to achieve the individual height profiles:

$$z1(x, y) = \frac{d}{2} + \Delta\phi(x, y) * \frac{\lambda}{4\pi\Delta n}$$

$$z2(x, y) = \frac{d}{2} - \Delta\phi(x, y) * \frac{\lambda}{4\pi\Delta n}$$

where d/2 is the nominal thickness of each plate, $\Delta\phi(x,y)$ is the designed phase delay profile (e.g., $\pi/2$ for quarter-wave, $\pi$ for half-wave delay between polarization), $\lambda$ is the wavelength and $\Delta n = n_e - n_o$ is the birefringence of the selected material. In this regard, the first plate 116 and second plate 118 assembly has a combined height of d and a phase delay given by:

$$\Delta\phi = 2\pi * \frac{\Delta n}{\lambda}\{2z(x, y) - d\}$$

By way of example, in the case of a 2 mm thick MgF$_2$ ($\Delta n$=0.0126) plate illuminated with laser light of wavelength $\lambda$=266 nm (e.g., laser light from Nd:Yag laser) the following is found for z1(x,y) and z2(x,y) (in μm):

$$z1(x,y) = 1000 + \Delta\phi(x,y) * 1.6694$$

$$z2(x,y) = 1000 - \Delta\phi(x,y) * 1.6694$$

In the case of a half-wave plate (i.e., $\Delta\phi=\pi$), the deviation of z from the nominal d/2 value is 5.244 μm corresponding with 19.71$\lambda$. It is noted that a similar calculation may be applied in the case of crystalline quartz ($\Delta n$=0.01078) and other like material.

It is noted herein that the particular profile shapes of the surfaces 117, 119 of plates 116, 118 may take on any general form required to correct aberrations and/or suppress an undesired signal (discussed further herein). The profile shapes may take on periodic or non-periodic form as a function of transverse position across the pupil plane.

Figure 1D:
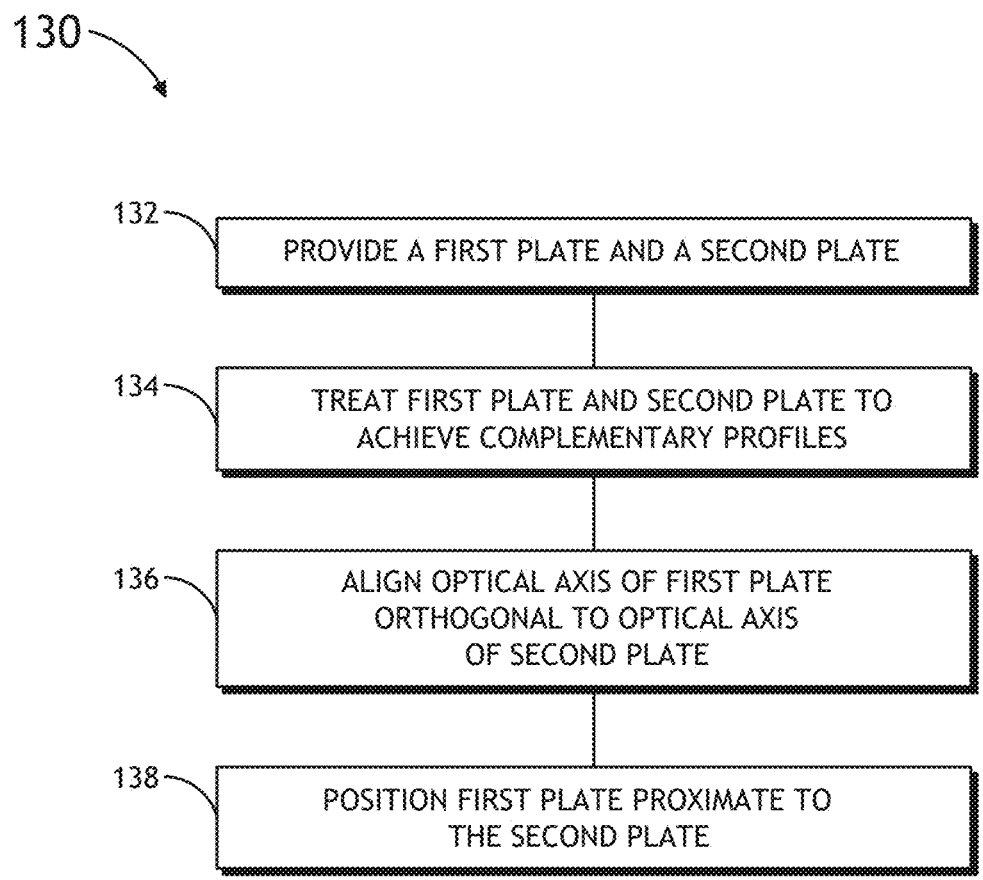
FIG. 1D illustrates a flow chart depicting a method of making the polarization control device, in accordance with one embodiment of the present invention.

FIG. 1D illustrates a flow diagram depicting a method 130 for forming the dual-sided polarization control device 102, in accordance with one or more embodiments of the present disclosure.

In a first step 132, a first plate 116 and a second plate 118 are provided. For example, a flat crystalline plate (e.g., MgF$_2$ or crystalline quartz plate) may be cut to form a first plate and a second plate. For the purposes of the present disclosure, plates having a surface roughness below 0.1$\lambda$ of the wavelength of illumination are considered 'flat.' By way of another example, the flat crystalline plate may be cut to form a first plate or second plate having any geometrical shape known in the art, such as, but not limited to, a square, a rectangle, a circle, and the like.

In a second step 134, the first plate 116 and the second plate 118 are treated to create complementary surface profiles 117, 119. It is noted herein that the surface profiles 117, 119 may be formed utilizing any suitable method known in the art. For example, the surface profiles 117, 119 may be formed utilizing one or more magnetorheological finishing (MRF) techniques. It is noted herein that MRF techniques may provide control of the surface profiles 117, 119 within approximately 1 nm. MRF is generally described by Menapace et al., "Magnetorheological Finishing for Imprinting Continuous Phase Plate Structure onto Optical Surfaces," Proceedings of SPIE, Vol. 5273 (2004), which is incorporated herein by reference in the entirety. MRF is also generally described by Tricard et al., "Continuous Phase Plate Polishing Using Magnetorheological Finishing," Proceedings of SPIE, Vol. 7062 (2008), which is incorporated herein by reference in the entirety. By way of another example, the surface profiles 117, 119 may be formed utilizing one or more etching techniques. By way of another example, the surface profiles 117, 119 may be formed utilizing one or more ion-beam machining techniques.

In a third step 136, the optical axis 121 of the first plate 116 is aligned orthogonal to the optical axis 123 of the second plate 118. As previously noted herein, the orthogonal alignment of the optical axes 121, 123 of the first and second plates 116, 118 provides for birefringence in the polarization control device 102.

In a fourth step 138, the first plate 116 is positioned proximate to the second plate 118. For example, the surface profile 117 of the first plate 116 and the surface profile 119 of the second plate 118 may be aligned and fit together utilizing a mechanically-coupling means (e.g., adhesive (e.g., glue, epoxy and the like) or mechanical device (e.g., clamp)). Further, an index-matching fluid may be used in the interface 120 between plates 116, 118.

It is noted herein that the polarization control device 102 of the present disclosure may be utilized to correct polarization aberrations imparted to an illumination beam by the optical elements of an optical system. For example, the polarization control device 102 may be used to correct polarization aberrations created by the surfaces/interfaces (e.g., non-normal reflective surfaces) of one or more optical elements of an optical system.

Figure 2:
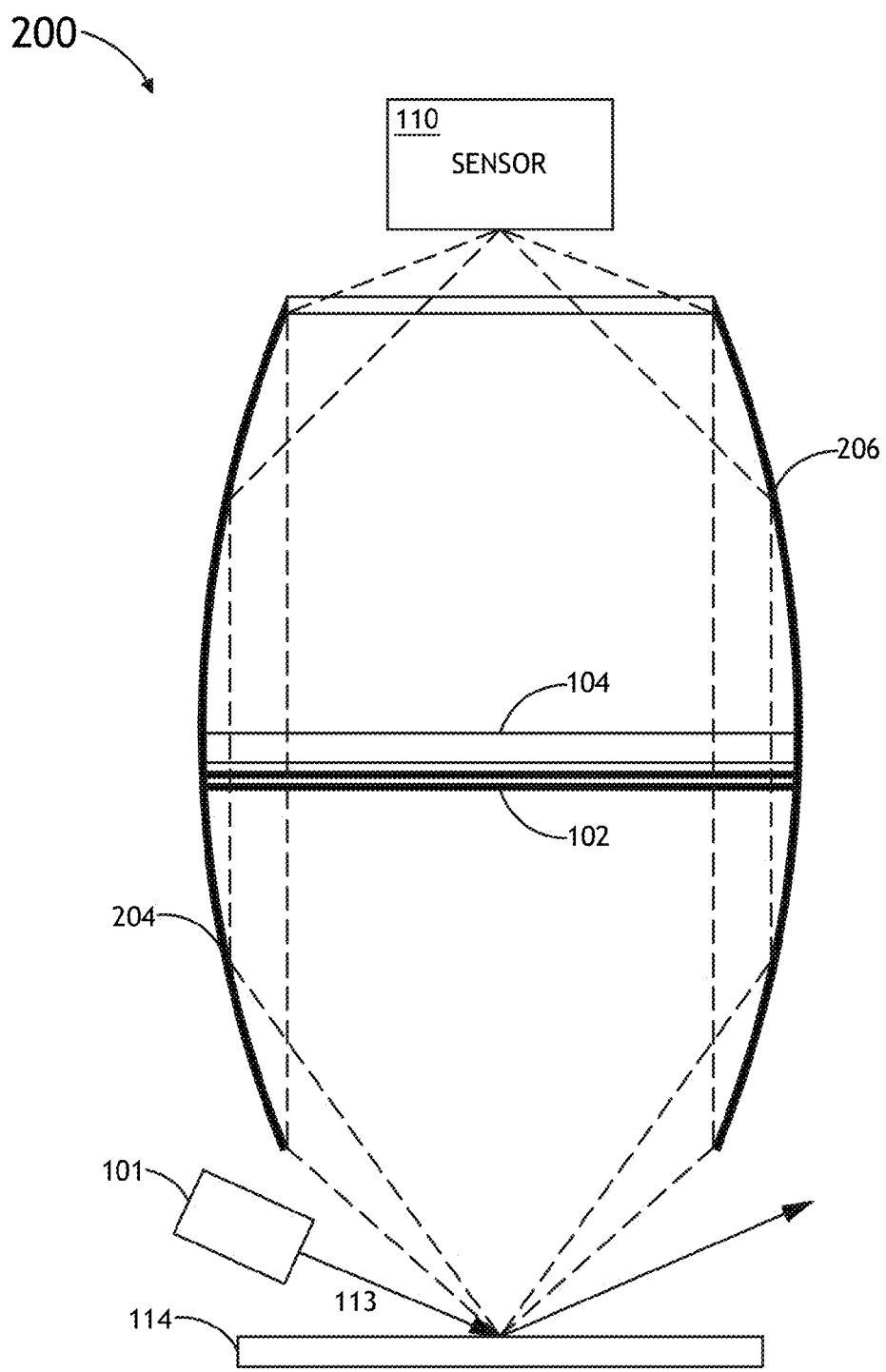
FIG. 2 illustrates a simplified schematic view of an inspection system with a parabolic collector implementing a polarization control device, in accordance with one embodiment of the present invention.

FIG. 2 illustrates a simplified schematic view of an inspection system 200 including one or more parabolic collectors and the polarization control device 102 used to correct aberrations within the inspection system 200, in accordance with one embodiment of the present disclosure. In one embodiment, inspection system 200 includes an illumination source 101 and a sensor 110, as described previously herein with respect to system 100. In another embodiment, the system 200 includes a polarization control device 102 and polarizer 104, which have also been generally described herein with respect to system 100. It is noted herein that the embodiments and implementations described previously herein with respect to the components and implementations of optical system 100 should be interpreted to extend to system 200.

In one embodiment, the inspection system 200 includes one or more parabolic collectors 204. In another embodiment, the volume within the one or more parabolic collectors 204 of system 200 may be filled with a low-scattering gas, such as, but not limited to, helium.

In one embodiment, the parabolic collector 204 is used to collect light from a sample over substantially large NA, as shown in FIG. 2. It is noted herein that, at the output, the parabolic collector 204 will display a substantially varying retardance over NA due to non-normal reflections at the collector 204 surface (e.g., mirror). It is further noted herein that collector-induced polarization changes may inhibit the ability of a given optical system to analyze polarization of collected light (e.g., using polarizer 104) or separate between different sources based on polarization distribution over NA.

In one embodiment, the polarization control device 102 is used in the NA plane to correct or reverse collector-induced changes. In this regard, the use of a polarization control device 102 allows for the use of a linear polarizer 104 (also positioned in the NA plane) to analyze a polarization state of collected light. In this regard, the polarization control device 102 may be constructed to have surface profiles 117, 119 suitable for correcting the collector-induced polarization changes. In this regard, the polarization control device 102 may include complementary individual surface profiles z1(x,y) and z2(x,y) suitable for continuously altering polarization across the NA of inspection system 200 so as to at least partially correct the collector-induced polarization changes of the system 200.

In another embodiment, after light is passed through the polarization control device 102, the light may then be converted back into image space and passed onto sensor 110. For example, in the case of an inspection system 200 including a first parabolic collector 204, light may be converted back into image space utilizing a second parabolic objection 206, as shown in FIG. 2. It is recognized herein that in some settings the dual-parabolic collector system 200 may replace an ellipsoid-shaped collector in some applications.

Figure 3:
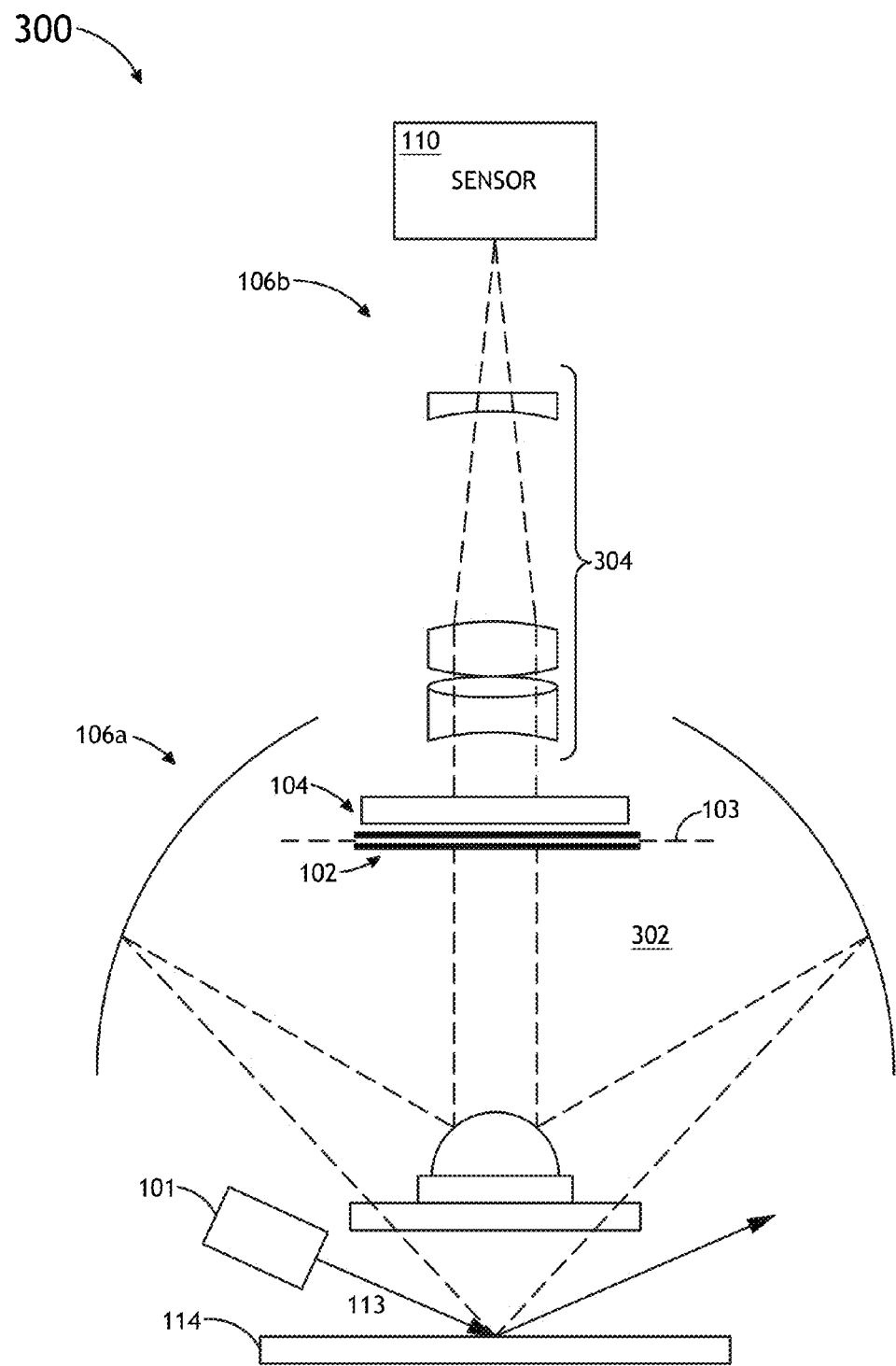
FIG. 3 illustrates a simplified schematic view of an inspection system with a Schwarzchild objective implementing a polarization control device, in accordance with one embodiment of the present invention.

FIG. 3 illustrates a simplified schematic view of an inspection system 300 including a Schwarzchild objective and the polarization control device 102 used to correct aberrations within the inspection system 300, in accordance with one embodiment of the present disclosure. In one embodiment, inspection system 300 includes an illumination source 101 and a sensor 110, as described previously herein with respect to system 100. In another embodiment, the system may include one or more lenses 304. For example, as shown in FIG. 3, the system 300 may include a tube lens. In another embodiment, the system 300 includes a polarization control device 102 and polarizer 104, which have also been generally described herein with respect to system 100. It is noted herein that the embodiments and implementations described previously herein with respect to the components and implementations of optical system 100 should be interpreted to extend to system 300.

In one embodiment, the inspection system 300 includes a Schwarzchild objective 302. In one embodiment, the Schwarzchild objective 302 is used to collect light from a sample 114 over substantially large NA, as shown in FIG. 3.

It is noted herein that as light passes through the Schwarzchild objective 302, each light ray undergoes two internal reflections (one before and one after the sample), as shown in FIG. 3. In the plane of incidence of a given light ray, the y-component is in-plane, with the x-component being out of plane. It is further noted that the x-component does not change during propagation through the objection, but the y-component is rotated by 180 degrees. As a result, the electric field vector is rotated after two reflections by an angle twice that of the azimuthal angle.

As in the case of system 300, the collector-induced polarization changes may inhibit the ability of a given optical system to analyze polarization of collected light (e.g., using polarizer 104) or separate between different sources based on polarization distribution over NA.

In one embodiment, the polarization control device 102 is used in the NA plane to correct or reverse collector-induced changes. In this regard, the use of a polarization control device 102 again allows for the use of a linear polarizer 104 (also positioned in the NA plane) to analyze a polarization state of collected light. In this regard, the polarization control device 102 may be constructed to have surface profiles 117, 119 suitable for correcting the polarization changes caused by the Schwarzchild objective 302. In this regard, the polarization control device 102 may include complementary individual surface profiles z1(x,y) and z2(x, y) suitable for continuously altering polarization across the NA of inspection system 300 so as to at least partially correct the polarization changes caused by the Schwarzchild objective 302 of the system 300.

In another embodiment, although not shown, the polarization control device 102 may be used within an inspection system that implements a refractive-based collector. In this regard, the polarization correct device 102 may at least partially correct polarization changes caused by a refractive-based collector on an inspection system.

Referring again to FIG. 1A generally, it is noted herein that the polarization control device 102 of the present disclosure may be utilized to discriminate between light sources based on the polarization of the light from the sources. In one embodiment, the polarization control device 102 in combination with the linear polarizer 104 may be used to suppress one or more unwanted light signals. For example, the polarization control device 102 in combination with the linear polarizer 104 may be used to enhance extinction of 'haze' associated with the surface of the sample 114. As such, the size of one or more signals associated with a defect or feature (e.g., particle) may be enhanced relative to the haze signal associated with the sample surface.

It is noted herein that in certain settings the polarization associated with the haze signal becomes elliptical. For example, in settings where the azimuthal angle of scattering is larger than +/−45°, the haze signal may have an elliptical polarization. In this situation, the haze signal cannot be suppressed by a simple linear polarizer. In addition, the direction of the main axis of the haze ellipse deviates from being orthogonal to the signal, which remains linear approximately along the radial direction.

In one embodiment, the polarization control device 102 may control polarization rotation as a function of position across the pupil plane so as to convert elliptically polarized light associated with haze to linearly-polarized light. In this regard, the polarization control device 102 may serve as a location-specific polarization retarder, which serves to impart varying levels of polarization rotation to the light as a function of position across the pupil plane 103 so as to produce linearly-polarized light in the same direction. In another embodiment, the polarization control device 102 again includes a first wave plate 116 and a second wave plate 118 including surface profiles 117, 119 which provide for a continuous variation of imparted polarization rotation as a function of position (e.g., x, y position) across the pupil plane 103. In another embodiment, the linear polarizer 104 may then be used to suppress the haze signal associated with the surface signal of the sample 114 as it exits the polarization control device 102 with linear polarization.

Figure 1E:
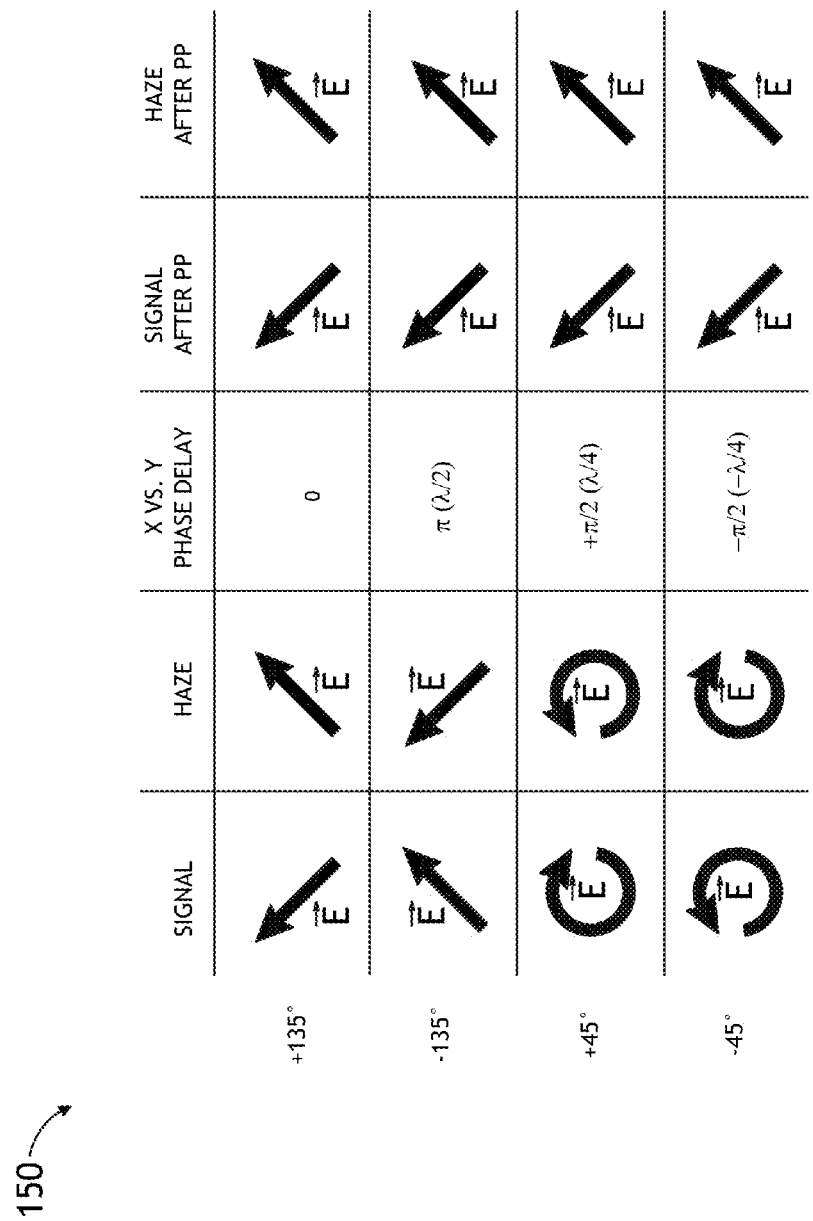
FIG. 1E illustrates a graph including a conceptual depiction of the direction of polarization for both a signal and the surface background, in accordance with one embodiment of the present invention.

FIG. 1E illustrates a graph 150 including a conceptual depiction of the direction of polarization for both a desired signal, such as a particle, and the surface background, in accordance with one embodiment of the present disclosure. As shown in FIG. 1E, graph 150 shows the direction of polarization for the signal and surface at various x-y phase delays (e.g., phase delays implemented by polarization control device) needed to transform polarization into the required state.

For example, at an azimuthal angle of +135°, a phase delay of 0 applied to the signal and haze, which are orthogonally polarized at +135°, results in no operation on the polarization state of the signal or the haze. As such, in this case, the signal and haze are orthogonally linearly polarized following the phase delay, allowing the linear polarizer 104 to suppress the haze signal.

By way of another example, at an azimuthal angle of −135°, an x-y phase delay of $\pi\lambda/2$ applied to the signal and haze, which have orthogonally polarized states opposite to the +135° case, results in the transformation of the polarization state of the signal and haze such that the polarization states are opposite to the initial polarization states. As such, in this case, the signal and haze are orthogonally linearly polarized following the phase delay, allowing the linear polarizer 104 to suppress the haze signal.

By way of another example, at an azimuthal angle of +45° C., an x-y phase delay of +π/2(λ4) applied to the signal and haze, which have opposite circularly polarized states in the +45° C. case, results in the rotation of the polarization states of the signal and the haze such that the polarization states are converted to orthogonal linear polarization states. As such, in this case, the signal and haze are orthogonally linearly polarized following the phase delay, allowing the linear polarizer 104 to suppress the haze signal.

By way of another example, at an azimuthal angle of −45° C., an x-y phase delay of −π/2(λ4) applied to the signal and haze, which have opposite circularly polarized states in the −45° C. case, results in the rotation of the polarization states of the signal and the haze such that the polarization states are converted to orthogonal linear polarization states. As such, in this case, the signal and haze are orthogonally linearly polarized following the phase delay, allowing the linear polarizer 104 to suppress the haze signal.

Using the principles outlined above in graph 150, the polarization control device 102 may be used to transform (or maintain) the polarization of the signal and/or haze in a spatially continuous manner (using the spatially varying phase delay profiles z1 and/or z2) across the pupil plane 103. Once the light of the signal and/or light of the haze have been transformed (or maintained) in nominally orthogonal linear states, the linear polarizer 104 may be used to suppress the haze signal. In this regard, the polarization control device 102 may serve to provide varying levels of phase retardation as a function position across the pupil plane 103 in order to impart the needed retardation to allow a polarizer 104 to suppress the haze (or any other unwanted signal) relative to the desired signal (e.g., scattering from particle).

FIG. 1F illustrates a conceptual illustration 160 of the conversion of elliptically polarized background signal, or haze signal, into linear polarized light, in accordance with one embodiment of the present invention. As shown in FIG. 1F, the phase retardation applied to light passing through the pupil plane 103 is a continuous function of location in the pupil. In this regard, once background light across the pupil is converted into linear polarization (with varying levels of phase retardation), the light may then easily blocked with a simple linear polarizer 104.

As shown in FIG. 1F, the path 166 depicts the application of a linear polarizer at fixed angle with respect to the phase plate. Further, path 168 conceptually depicts a phase plate selected to produce optimized SNR. In this case, background polarization 164 is "shrunk," or reduced to almost linear polarization, so that the linear polarizer 104 operates more effectively on the light. Further, path 170 conceptually depicts the use of a linear polarizer with location specific preferred polarization angle.

In one embodiment, the example depicted in FIG. 1F may correspond to illumination with an azimuthal angle of 90°. In this regard, the signal 162 (e.g., particle signal) has linear polarization along a first coordinate axis, while the haze 164, or background signal, is elliptically polarized and titled from the first axis (e.g., vertical axis) by approximately 30°. It is noted herein that the description related to FIGS. 1E and 1F are not limiting and should be interpreted merely as illustrative.

Figure 4:
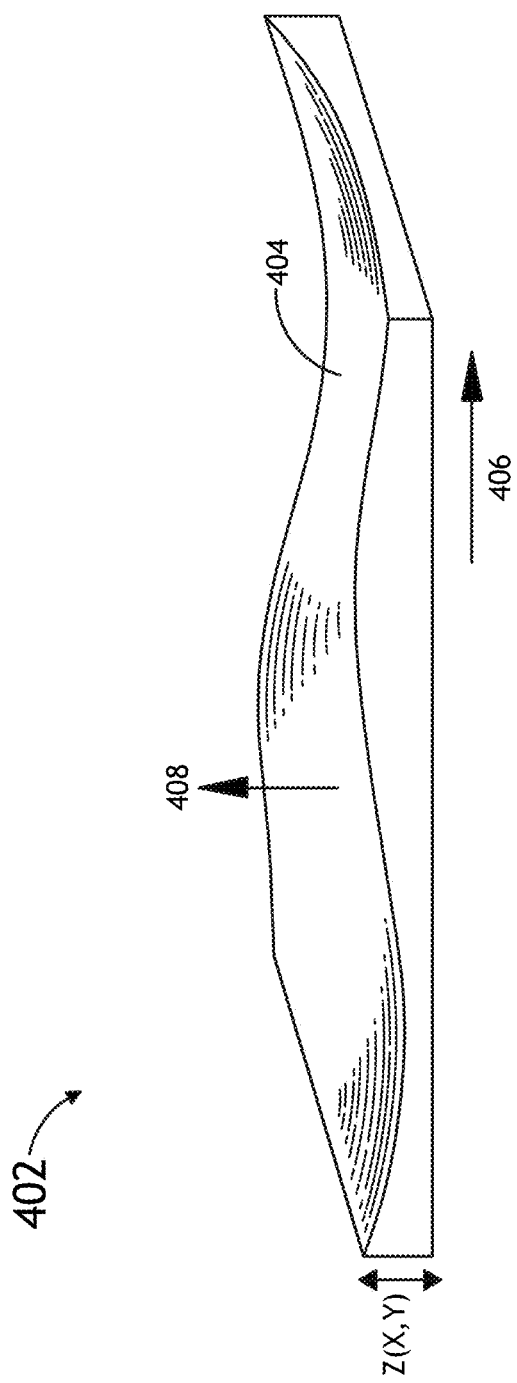
FIG. 4 illustrates a schematic view of a single-plate polarization control device, in accordance with one embodiment of the present invention.

While much of the disclosure has focused on a polarization control device 102 including two plates 116, 118, it is noted herein that this is not a limitation of the present invention. FIG. 4 illustrates a simplified schematic view of a single-plate polarization control device 402, in accordance with an alternative embodiment of the present disclosure. In this regard, it is noted herein that the polarization control device 402 may be used in a manner similar to the polarization control device 102 described previously herein. As such, all of the various embodiments and implementations of polarization control device 102 should be interpreted to extend to the polarization control device 402. In one embodiment, the single-plate polarization control device 402 includes a surface profile 404, whereby the height z varies as a function of x-position and y-position. In another embodiment, the polarization control device 402 includes an optical axis 406, which may be arranged orthogonal to the illumination direction 408. It is noted herein that the use of a single plate in the polarization control device 102 may be particularly advantageous in settings where aberration correction (which may be created by a single plate) are not required.

Figure 5A:
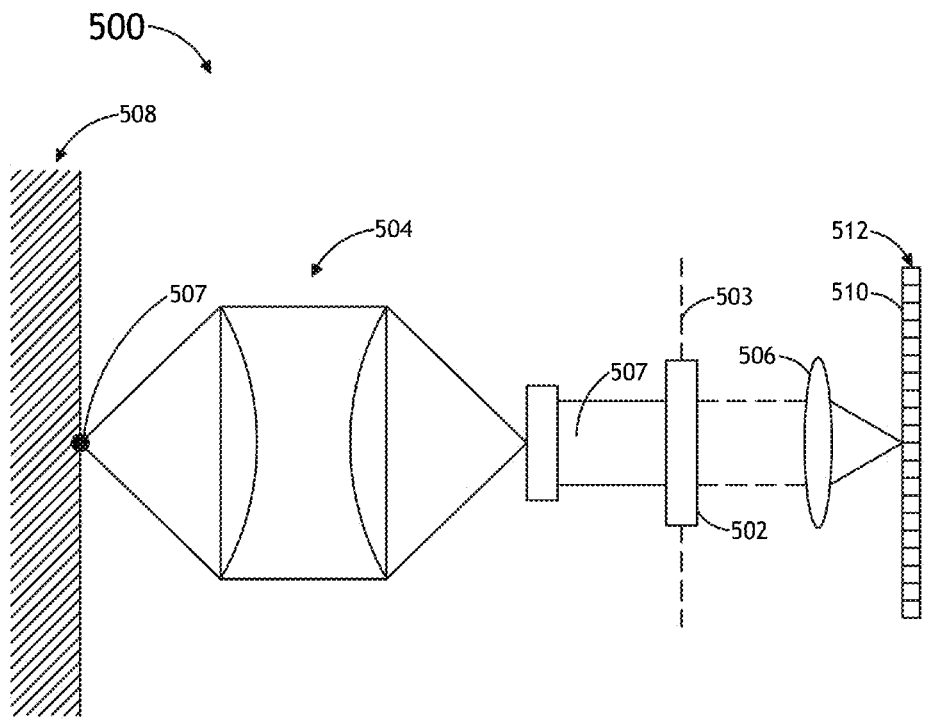
FIG. 5A illustrates a simplified schematic view of an optical system implementing a PSF control device, in accordance with one embodiment of the present invention.

FIG. 5A illustrates an optical system 500 equipped with a point spread function control device 502 suitable for modifying point spread function (PSF) of the system 500, in accordance with one embodiment of the present disclosure. It is noted herein that the ability to control PSF may allow for the increase in the amount of energy collected per pixel within a given detector, thereby providing increased sensitivity within an optical system and/or reduced light source (e.g., laser) power requirements.

In one embodiment, the system 500 provides for controlling polarization rotation as a function of position across the pupil plane 503. In another embodiment, the system 500 provides for imparting an optical delay to the illumination as a function of position across the pupil plane 503. In this regard, the system 500 may modify the PSF of the illumination of the optical system 500 so that the amount of illumination energy received by one or more pixels matches the size of the pixels size of the detector array 512. In this regard, the PSF control device 502 may serve to enhance or maximize the amount of optical energy received by one or more pixels 510 of the detector array 512.

Figure 5B:
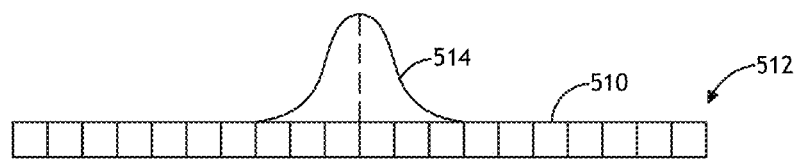
FIG. 5B illustrates a conceptual view of a point spread function overlapping multiple pixels of a detector array, in accordance with one embodiment of the present invention.
Figure 5C:
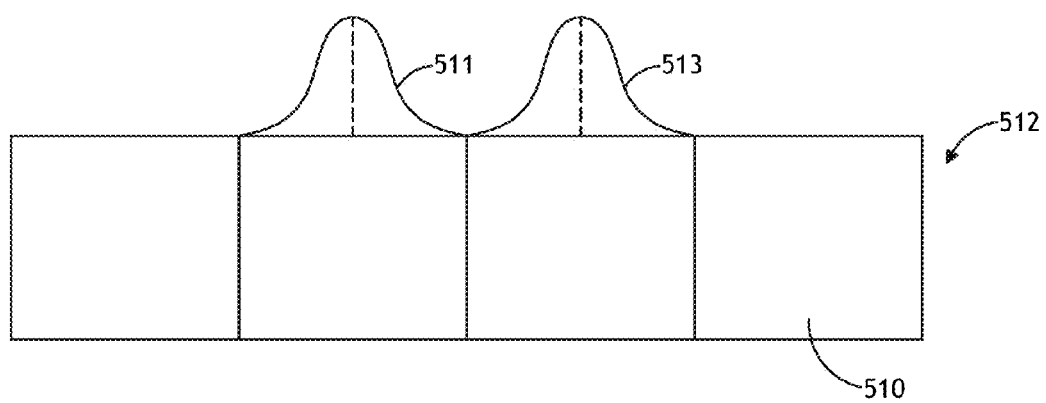
FIG. 5C illustrates a conceptual view of split point spread functions from a single illumination source matched to the size of the pixels of a detector array, in accordance with one embodiment of the present invention.

For example, as shown in FIG. 5B, an untreated illumination beam may have a PSF 514 that spreads across multiple pixels 510 of the detector array 512. As a result, the amount of optical energy received by a single pixel is sub-optimal and further requires the reading of multiple pixels for a single detection. In one embodiment, as shown in FIG. 5C, the PSF control device 502 (e.g., phase plate device 535 or optical delay device 537) may control polarization rotation or the optical delay in order to control the degree of coherency to form two point spread functions 511, 513 which are incoherent and act to enhance the amount of energy received by a given pixel 510.

Referring again to FIG. 5A, in one embodiment, the system 500 includes a set of refractive optics 504 configured to collect light scattered from a feature 507 on sample 508. For example, the refractive optics 504 may include a set of refractive collection elements. For instance, the set of refractive collection elements may include, but is not limited to, a catadioptric objective. In another embodiment, the system 500 includes one or more lenses 506 configured to focus the illumination onto one or more pixels 510 of a detector array 512. It is noted herein that the detector array 512 is depicted as being one-dimensional merely for descriptive convenience and such a depiction should not be interpreted as a limitation on the present invention. For example, the detector array 512 may include, but is not limited to, a two-dimensional detector array made up of an n×m grid of pixels.

Figure 5D:
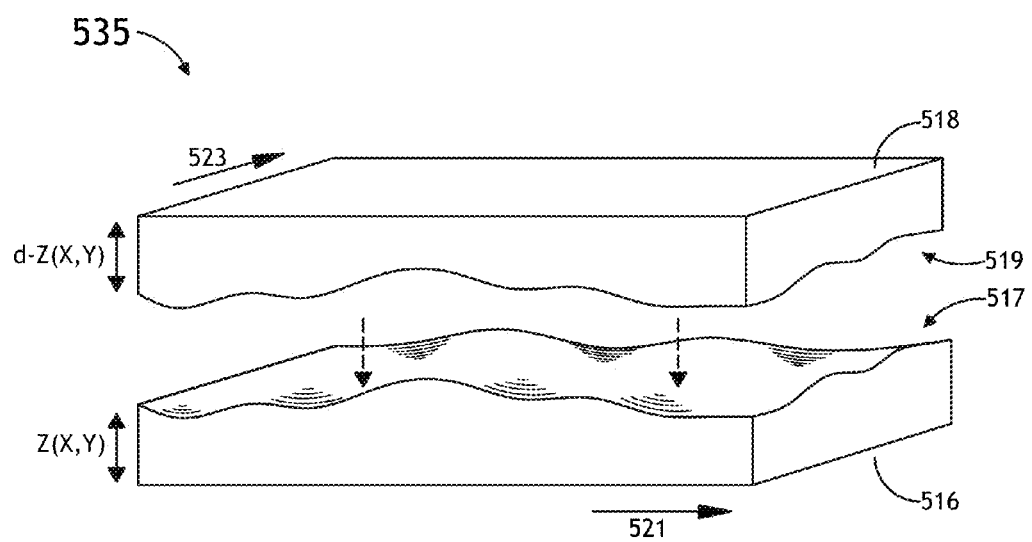
FIG. 5D illustrates a schematic view of a point spread function control device, in accordance with one embodiment of the present invention.

In one embodiment, the PSF control device 502 of system 500 is a polarization control device 535, as shown in FIG. 5D. In one embodiment, the polarization control device 535 includes a pair of phase plates 516 and 518, as depicted in FIG. 5D. In an alternative embodiment, the polarization control device 535 may include a single plate. In one embodiment, the polarization control device 535 may modify PSF of the optical system 500 via the modulation of the phase of light as a function of position across the pupil plane 503. In another embodiment, the polarization control device 535 may modify PSF of the optical system 500 via the modulation of the degree of coherence as a function of position across the pupil plane 503. It is noted herein that the polarization control device 535 may be used to improve the amount of energy collected by an individual pixel 510 of detector 512.

In this regard, the introduction of controlled polarization rotation with polarization control device 535 may split light incident on the detector array 512 into two light distributions of orthogonal polarizations corresponding with two point spread functions (e.g., 511 and 513) in the image plane of the detector array 512. In another embodiment, the two point spread functions in the image plane of the detector array 512 may be added incoherently, which may help minimize diffraction ringing effects while reducing the spread of each PSF, resulting in higher enclosed energy in a given detector pixel 510. In another embodiment, the two point spread functions in the image plane of the detector array 512 may be added coherently.

In one embodiment, the plates 516 and 518 of the polarization control device 535 have complementary surface profiles 517, 519. In another embodiment, the first plate 516 of the device 515 has a first optical axis 521. Further, the second plate 518 has an optical axis 523, which is oriented orthogonal to the first optical axis 521. In addition, the optical axis 521 of the first plate 518 and the optical axis 523 of the second plate 518 may be oriented orthogonal to the direction of illumination propagation through the device 535.

It is noted that the general construction of polarization control device 535 and the considerations taken into account when constructing the device 535 are similar to that for the polarization control device 102. It is noted, however, that the polarization control device 535 is implemented within an optical system in order to control PSF, while the polarization control device 102 is implemented within an optical system to correct polarization aberrations and/or improve the signal-to-noise ratio in the system. As such, while the construction of devices 102 and 535 are similar, it is not necessarily the case (although it is possible) that the various parameters (e.g., surface profiles, interface distance, thickness of component plates, thickness of overall device and the like) of the devices 102 and 535 will be the same.

Figure 5E:
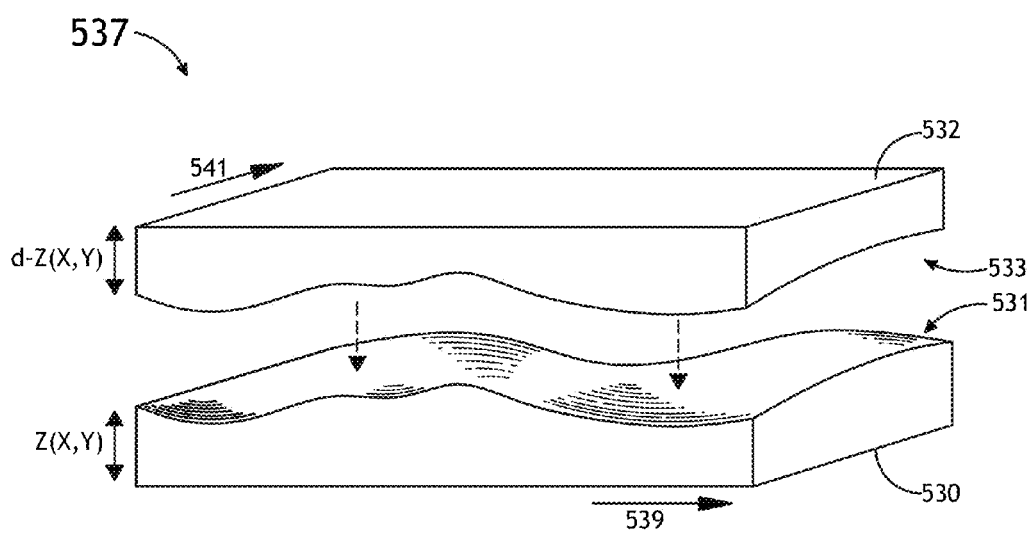
FIG. 5E illustrates a schematic view of a point spread function control device, in accordance with one embodiment of the present invention.

In another embodiment, the PSF control device 502 of system 500 includes an optical delay device 537, as shown in FIG. 5E. In one embodiment, the optical delay control device 537 includes one or more plates 530, 532 as depicted in FIG. 5E. It is noted herein that the plates of the optical delay control device 537 of FIG. 5E may be formed in a manner similar to the plates described throughout the presentation. It is noted, however, that the optical delay control device 537 of FIG. 5E may include a plate thickness variation on the order of 1-3 mm, which is larger than a laser pulse length/temporal coherence length.

In one embodiment, the plates 530 and 532 of the optical delay control device 537 have complementary surface profiles 531, 533. In another embodiment, the first plate 530 of the device 537 has a first optical axis 539. Further, the second plate 532 has an optical axis 541, which is oriented orthogonal to the first optical axis 539. In addition, the optical axis 539 of the first plate 530 and the optical axis 541 of the second plate 518 may be oriented orthogonal to the direction of illumination propagation through the optical delay control device 537.

The operation of the optical delay control device 537 may be described as follows. In one embodiment, a subset A of pupil points may have optical delay DA (i.e., all points in a subset have some delay), while subset B has an optical delay DB. Therefore, pupil points in subset B have an optical delay with respect to points in subset A of (DB−DA). In the event that (DB−DA) is greater than the coherence length of illuminated light (or simply larger than the pulse width in the case of a pulsed light source), then subsets A and B will effectively be incoherent with respect to each other (while points within each subset maintain coherence among them). In this case, subsets A and B will create independent distributions in an image plane by adding incoherently, and achieve effects similar to that of subsets A and B having orthogonal polarizations. It is noted herein that implementation of an optical delay may be most straightforward from the standpoint of reduced manufacturing tolerances, while also allowing for multiple incoherent subsets (as opposed to allowing for only two distributions in the case of the polarization rotation approach). On the other hand, for a typical pulse width (e.g. 20 ps), the optical delay control device 537 would have to have thickness variations on the order of a few millimeters, which is thicker than that needed for the polarization rotational plate 535. As such, transitional regions within the optical delay control device 537 would display large local surface tilts when compared to polarization rotation plate 535.

It is recognized herein that the PSF plate (e.g., phase plate 535 or optical delay plate 537) may be used in conjunction with the polarization control device 102 described previously herein. For example, the polarization control plate 102 may be used to improve signal-to-noise ratio by, for example, suppressing haze of the sample 508 surface relative to the scattering signal from the defect 507. Further, the polarization control device 102 may be used to correct polarization aberrations within the given optical system. In contrast, the PSF control device 502 (e.g., polarization rotation control device 535 or optical delay control device 537) may be used to control the PSF of the illumination and enhance or match the PSF to the one or more pixels 510 of detector 512.

In another embodiment, a given optical system may implement both the polarization control device 102 and the PSF control device 502 in an effort to simultaneously improve signal-to-noise, correct aberrations and enhance PSF matching to the given detector array.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A polarization control apparatus comprising:
a first wave plate having a first surface profile; and
a second wave plate having a second surface profile complementary to the first surface profile;
the optical axis of the first wave plate substantially orthogonal to the optical axis of the second wave plate;
the first wave plate and the second wave plate positioned so as to substantially align the first surface profile with the second surface profile and maintain a constant thickness of an assembly of the first wave plate and second wave plate,
the assembly of the first wave plate and the second wave plate being configured to control polarization rotation as a continuous function of transverse position across a pupil plane of an optical system,
the first profile of the first wave plate being separated from the second profile of the second wave plate by a selected distance so as to limit wave front distortion of illumination passing through the first wave plate and second wave plate below a selected level.

2. The apparatus of claim 1, wherein the first wave plate and second wave plate control polarization rotation as a function of transverse position in the pupil plane of the optical system by controlling a level of retardance as a function of transverse position in the pupil plane of the optical system.

3. The apparatus of claim 1, wherein the first wave plate is operably coupled to the second wave plate so the first profile of the first wave plate is separated from the second profile of the second wave plate by a selected distance.

4. The apparatus of claim 3, wherein the first wave plate is affixed to the second wave plate so the first profile of the first wave plate is separated from the second profile of the second wave plate by a selected distance.

5. The apparatus of claim 3, wherein the first wave plate is mechanically coupled to the second wave plate so the first profile of the first wave plate is separated from the second profile of the second wave plate by a selected distance.

6. The apparatus of claim 1, wherein an index-matching material is disposed between the first profile of the first wave plate and the second profile of the second wave plate.

7. The apparatus of claim 1, wherein at least one of the first wave plate and the second wave plate is formed from an optical crystalline material.

8. The apparatus of claim 7, wherein the optical crystalline material comprises:
at least one of crystalline quartz and magnesium fluoride.

9. The apparatus of claim 1, wherein one or more surface profiles of at least one of the first wave plate and the second wave plate are controlled via magnetorheological finishing.

10. The apparatus of claim 1, wherein at least one of the first wave plate and the second wave plate comprises an etched plate.

11. The apparatus of claim 1, wherein at least one of the first wave plate and the second wave plate comprises an ion beam machined plate.

12. The apparatus of claim 1, wherein the polarization control device is configured to correct polarization aberrations caused by one or more optical elements of the optical system.

13. The apparatus of claim 1, wherein the polarization control device is configured to suppress one or more selected light signals.

14. The apparatus of claim 13, wherein the polarization control device is configured to suppress a haze signal associated with a surface of a sample.

15. An optical system for controlling polarization comprising:
an illumination source configured to illuminate a surface of a sample;
a set of collection optics configured to collect illumination from the surface of a sample;
a polarization control device positioned substantially at a pupil plane of the optical system, the polarization control device including:
a first wave plate having a first surface profile;
a second wave plate having a second surface profile complementary to the first surface profile;
the optical axis of the first wave plate substantially orthogonal to the optical axis of the second wave plate, the optical axis of the first wave plate and the optical axis of the second wave plate substantially orthogonal to a direction of illumination propagation through the polarization control device;
the first wave plate and the second wave plate positioned so as to substantially align the first surface profile with the second surface profile and maintain a constant thickness of an assembly of the first wave plate and second wave plate;
the assembly of the first wave plate and the second wave plate being configured to control polarization rotation as a function of transverse position in a pupil plane of the optical system; and
a linear polarizer configured to receive illumination transmitted through the polarization control device; and
a sensor configured to detect illumination transmitted through the linear polarizer.

16. The system of claim 15, wherein the first wave plate and second wave plate control polarization rotation as a function of transverse position in the pupil plane of the optical system by controlling a level of retardance as a function of transverse position in the pupil plane of the optical system.

17. The system of claim 15, wherein the first wave plate is operably coupled to the second wave plate so the first profile of the first wave plate is separated from the second profile of the second wave plate by a selected distance.

18. The system of claim 17, wherein the first wave plate is affixed to the second wave plate so the first profile of the first wave plate is separated from the second profile of the second wave plate by a selected distance.

19. The system of claim 17, wherein the first wave plate is mechanically coupled to the second wave plate so the first profile of the first wave plate is separated from the second profile of the second wave plate by a selected distance.

20. The system of claim 15, wherein an index-matching material is disposed between the first profile of the first wave plate and the second profile of the second wave plate.

21. The system of claim 15, wherein at least one of the first wave plate and the second wave plate is formed from an optical crystalline material.

22. The system of claim 21, wherein the optical crystalline material comprises:
at least one of crystalline quartz and magnesium fluoride.

23. The system of claim 15, wherein one or more surface profiles of at least one of the first wave plate and the second wave plate are controlled via magnetorheological finishing.

24. The system of claim 15, wherein at least one of the first wave plate and the second wave plate comprises an etched plate.

25. The system of claim 15, wherein at least one of the first wave plate and the second wave plate comprises an ion beam machined plate.

26. The system of claim 15, wherein the optical system is an inspection system.

27. The system of claim 15, wherein the optical system is a high NA ultraviolet inspection system.

28. The system of claim 15, wherein the polarization control device is configured to correct one or more aberrations caused by one or more optical elements of an optical system.

29. The system of claim 28, wherein the optical system includes a parabolic collector.

30. The system of claim 28, wherein the optical system includes a Schwarzchild objective.

31. The system of claim 28, wherein the optical system includes a refractive based collector.

32. The system of claim 15, wherein the polarization control device and linear polarizer are configured to suppress one or more selected light signals.

33. The system of claim 32, wherein the polarization control device and linear polarizer are configured to suppress a haze signal associated with a surface of a sample.

* * * * *